(12) United States Patent
Jacobsen et al.

(10) Patent No.: US 6,440,088 B1
(45) Date of Patent: Aug. 27, 2002

(54) HYBRID CATHETER GUIDE WIRE APPARATUS AND METHOD

(75) Inventors: Stephen C. Jacobsen; Clark Davis, both of Salt Lake City; John Lippert, Park City, all of UT (US)

(73) Assignee: Precision Vascular Systems, Inc., West Valley City, UT (US)

(*) Notice: Subject to any disclaimer, the term of this patent is extended or adjusted under 35 U.S.C. 154(b) by 0 days.

(21) Appl. No.: 08/975,769

(22) Filed: Nov. 21, 1997

Related U.S. Application Data

(63) Continuation-in-part of application No. 08/653,199, filed on May 24, 1996, now Pat. No. 5,690,120.

(51) Int. Cl.[7] .................................................. A61B 5/00
(52) U.S. Cl. ...................................... 600/585; 604/523
(58) Field of Search .................................. 600/585, 435, 600/434; 604/95, 96, 280, 281, 282, 523–524, 525, 528, 529, 530, 531

(56) References Cited

U.S. PATENT DOCUMENTS

| 5,040,543 | A | | 8/1991 | Badera et al. |
| 5,063,935 | A | * | 11/1991 | Gambale ..................... 600/585 |
| 5,437,288 | A | | 8/1995 | Schwartz et al. |
| 5,573,520 | A | | 11/1996 | Schwartz et al. |
| 5,666,969 | A | | 9/1997 | Urick et al. |

FOREIGN PATENT DOCUMENTS

WO    WO 93/04722    3/1993

* cited by examiner

*Primary Examiner*—Kevin Shaver
*Assistant Examiner*—Pamela Wingood

(57) ABSTRACT

A hybrid catheter guide wire includes an elongate solid body having a tapered distal end over which is disposed a tubular section—about which a catheter may be threaded for guidance to a target location in a vasculature passageway of a body. Cuts are formed either by saw-cutting, laser cutting or etching at spaced-apart locations along at least a portion of the tubular section to increase its lateral flexibility, while maintaining its rotational torquability, and to control the direction and degree of flexure.

36 Claims, 1 Drawing Sheet

HYBRID CATHETER GUIDE WIRE APPARATUS AND METHOD

This is a continuation-in-part application of Ser. No. 08/653,199, filed May 24, 1996 now U.S. Pat. No. 5,690,120.

BACKGROUND OF THE INVENTION

This invention relates to a hybrid catheter guide wire apparatus with improved torque and flexure characteristics.

Catheter guide wires have been used for many years to "lead" or "guide" catheters to desired target locations in the human body's vasculature. The typical guide wire is from about 135 centimeters to 195 centimeters in length, and is made from two primary pieces—a stainless steel core wire, and a platinum alloy coil spring. The core wire is tapered on the distal end to increase its flexibility. The coil spring is typically soldered to the core wire at a point where the inside diameter of the coil spring matches the outside diameter of the core wire. Platinum is selected for the coil spring because it provides radiopacity for X-ray viewing during navigation of the guide wire in the body, and it is biocompatible. The coil spring also provides softness for the tip of the guide wire to reduce the likelihood of puncture of the anatomy.

Navigation through the anatomy is achieved by viewing the guide wire in the body using X-ray fluoroscopy. The guide wire is inserted into a catheter so the guide wire protrudes out the end, and then the wire and catheter are inserted into a vessel or duct and moved therethrough until the guide wire tip reaches a desired vessel or duct branch. The proximal end of the guide wire is then rotated or torqued to point the curved tip into the desired branch and then advanced further. The catheter is advanced over the guide wire to follow or track the wire to the desired location, and provide additional support for the wire. Once the catheter is in place, the guide wire may be withdrawn, depending upon the therapy to be performed. Oftentimes, such as in the case of balloon angioplasty, the guide wire is left in place during the procedure and will be used to exchange catheters.

As the guide wire is advanced into the anatomy, internal resistance from the typically numerous turns, and surface contact, decreases the ability to advance the guide wire further. This, in turn, may lead to a more difficult and prolonged procedure, or, more seriously, failure to access the desired anatomy and thus a failed procedure. A guide wire with both flexibility and good torque characteristics (torsional stiffness) would, of course, help overcome problems created by the internal resistance.

Among the approaches suggested in the prior art for increasing the flexibility of the tip of a guide wire is that of cutting axially spaced grooves in and near the tip, with the depths of the grooves increasing toward the tip. See U.S. Pat. No. 5,437,288. The use of cuts to increase flexibility on one side only of a tubular guide wire is disclosed in U.S. Pat. No. 5,411,483.

SUMMARY OF THE INVENTION

It is an object of the invention to provide an improved catheter guide wire apparatus.

It is also an object of the invention to provide such apparatus which exhibits both torsional stiffness, bending flexibility, and longitudinal strength.

It is a further object of the invention to provide such apparatus which is simple in design and construction.

It is another object of the invention, in accordance with one aspect thereof, to provide a catheter guide wire apparatus with improved flow directability characteristics.

The above and other objects of the invention are realized in a specific illustrative embodiment of a hybrid catheter guide wire apparatus formed of a thin elongate solid body of material which tapers or is otherwise reduced in diameter to a thinner distal termination, and a thin elongate tubular body of material disposed co-linearly to the distal end of the solid body to circumscribe at least a portion thereof. The tubular body, which is constructed to have greater lateral flexibility than the solid body, while retaining torsional stiffness, is attached at its proximal end to the solid body, or at its distal end to the solid body, or at both ends to the solid body. Cuts may be formed in the tubular body, transversely thereof to give the guide wire flexibility without significantly reducing torsional stiffness or strength.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1:
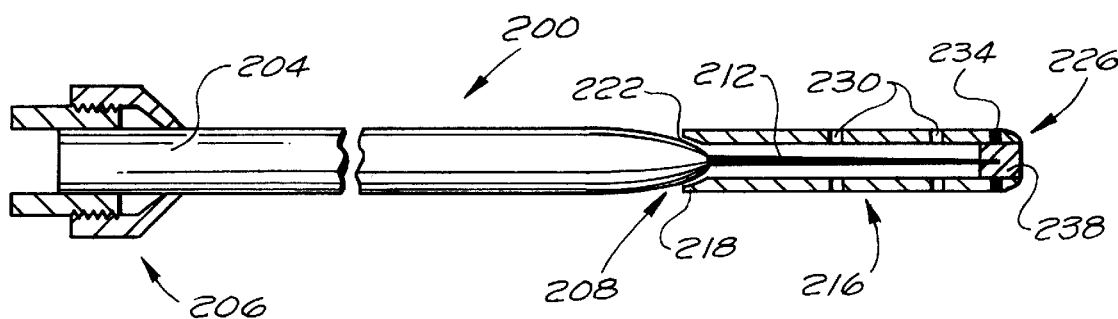
FIG. 1 shows a side, fragmented, partially cross-sectional view of one embodiment of a catheter guide wire apparatus made in accordance with the principles of the present invention.

FIG. 1 shows a side, fragmented, partially cross-sectional, view of one embodiment of a hybrid guide wire 200 made in accordance with the present invention. A pin vise type torquing chuck 206 is shown attached to a proximal end 204 in the usual manner. The guide wire 200 also includes a distal end 208 which tapers (but could be reduced more abruptly) to a thin, narrow section 212. Mounted over the thin, narrow section 212 is a tubular section 216 whose proximal end 218 abuts the sloping portion 222 of the distal end 208 of the proximal guide wire segment, and whose distal end 226 is rounded to reduce the chance of damage and trauma to the vasculature when the guide wire is being threaded therein.

Advantageously, the guide wire 200 is constructed of stainless steel and the tubular section 216 is constructed of nickel-titanium alloy to provide for greater lateral flexibility. Additional lateral flexibility can be achieved by providing cuts, slots, gaps or openings 230 along at least a portion of the exterior surface of the tubular section 216. These cuts may be formed by saw cutting (e.g., diamond grit embedded semiconductor dicing blade), etching (for example using the etching process described in U.S. Pat. No. 5,106,455), laser cutting, or electron discharge machining. Provision of the cuts in the tubular section increases lateral flexibility in the guide wire, while maintaining torsional stiffness.

The thin, narrow section 212 of the guide wire 200 is shown in the drawing as being an extension of the larger part of the body and thus made of the same material, the section 212 could also be made of a carbon fiber or polymer strand, attached to the larger part of the body 200 (for example, by a suitable adhesive), and this would provide excellent longitudinal strength with very little lateral stiffness.

Advantageously, the diameter of the larger proximal part of the catheter guide wire 200 could be from about 0.008 to 0.038 inches, as could be the outside diameter of the tubular section 216. A preferred diameter is 0.014 inches, with the interior diameter of the hollow of the tubular section 216 being about 0.0085 inches. Of course, the outside diameter of the tubular section 216 could be greater or less than that of the larger part of the catheter guide wire 200.

The distal end of the tubular section 216 may be preshaped with a curve to allow for directing the guide wire around curves and bends. Also formed on the distal end 226 of the tubular section 216 is a radiopaque or MRI sensitive marker or band 234. The band 234 may be gold or platinum alloy (for X-ray fluoroscopy) or gadolinium or dysprosium, or compounds thereof (for MRI) and may be formed on the distal end 226 by deposition, wrapping or use of shape memory alloy (NiTi) effect to "lock" the band around the end. Alternatively, a radiopaque or MRI sensitive plug 238 could be disposed in the distal end 226 of the tubular section 216 and attached to the distal end of the thin, narrow section 212 of the solid body portion of the guide wire 200 (or to the carbon fiber or polymer strand) to both serve as a marker and to assist in holding the tubular section 216 in place over the thin, narrow section 212. Glue or other adhesives could also be used to hold the tubular section 216 in place, including radiopaque glue. Finally, a radiopaque or MRI sensitive coil or flexible plastic tube could be disposed about the narrow section 212 of the guide wire, within the tubular section 216, to provide a much larger, more readily viewable marker.

To improve slidability of the guide wire 200 in a vasculature passageway, the exterior surface of the guide wire, including tubular section 216, could be sandblasted, beadblasted, sodium bicarbonate-blasted, electropolished and/or coated with a lubricious coating such as a silicon based oil and/or polymer or a hydrophilic polymer. Alternatively, a sleeve could be disposed over the entire length of the guide wire where the sleeve could also be made of a lubricious, hydrophilic polymer, or other polymer and then coated.

Cuts 230 of various shapes may be selectively spaced along and about the tubular section 216 to provide for selective bending of the tubular section, while maintaining good torsional stiffness. For example, the cuts could be formed at circumferentially-spaced locations about the tubular section 216 and could be formed with various shapes, the depth and thickness of which could be chosen to again allow for preferential bending of the section.

In the embodiment of FIG. 1, the guide wire 200 can be made "flow directable" by providing a highly flexible distal end. "Flow directability" means that the distal end of the guide wire tends to "flow" with the blood around curves and bends in a vasculature passageway.

Figure 2A:
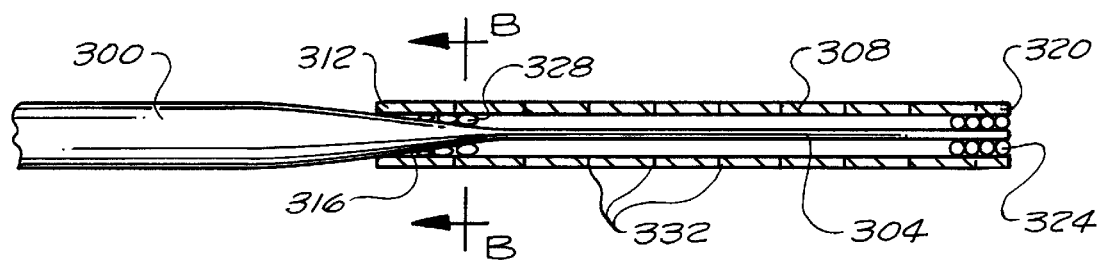
FIGS. 2A and 2B show respectively a side, fragmented, partially cross-sectional view, and an end cross-sectional view taken along lines B—B, of another embodiment of the present invention.
Figure 2B:
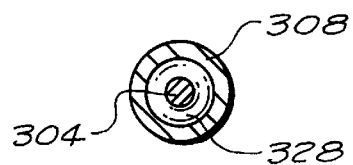

FIGS. 2A and 2B show respectively a side, fragmented, partially cross-sectional view and an end cross-sectional view of another embodiment of the hybrid catheter guide wire apparatus of the present invention. There shown is a guide wire 300 which tapers (but may be abruptly reduced) at its distal end to a thin, narrow section 304. A tubular section 308 is mounted about the thin, narrow section 304, as with the FIG. 1 embodiment, so that its proximal end 312 abuts the sloping portion 316 (or other portion) of the distal end of the guide wire 300, and its distal end 320 is generally contiguous with the termination of the thin, narrow section 304. Disposed about the termination of the thin, narrow section 304 and within the distal end 320 of the tubular section 308 is a platinum, radiopaque coil 324. The coil 324 is held in place to the termination of the thin, narrow section 304 and the distal end 320 of the tubular section 308 by a suitable adhesive.

Another coil 328 is disposed about the sloping portion 316 of the guide wire 300 near the proximal end 312 of the tubular section 308, to serve as a spacer or bushing between the tubular section 308 and the guide wire 300. Advantageously, the coil 328 is made of platinum. The coil 328 is held in place by a suitable adhesive. Thus, the tubular section 308 is held in place about the thin, narrow section 304 by adhesive both at the proximal end 312 and the distal end 320.

The coil 324 could be extended rearwardly, or the coil 328 could be extended forwardly, to loosely fill the space between the narrow section 304 and tubular section 308 and thus provide greater viewability of the radiopaque marker. Alternatively, an MRI sensitive or radiopaque flexible tube could be disposed in the space.

As with the FIG. 1 embodiment, the guide wire 300 advantageously is constructed of stainless steel while the tubular section 308 is constructed of nickel-titanium alloy. Cuts, slots, gaps or openings 332 may be formed along at least a portion of the exterior surface of the tubular section 308 to achieve additional desired lateral flexibility.

The dimensions of the embodiment of FIGS. 2A and 2B may be similar to those of the FIG. 1 embodiment. A typical length of the tubular section 308 is from 8 to 20 centimeters. Additionally, the distal end of the tubular section 308 may be preshaped with a curve to allow for directing the guide wire around curves and bends, and may be formed to include MRI sensitive markers or bands (in addition to the radiopaque coils 324 and 328), as with the FIG. 1 embodiment.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A hybrid catheter guide wire for introduction into a vessel pathway to guide a catheter to a predetermined location, comprising a thin elongate solid body of material including a thinner distal termination section, and a thin elongate tubular body of material having a proximal end and a distal end, and attached co-linearly at its proximal and distal ends to the solid body to circumscribe at least a portion of the distal termination section of the solid body, at least some portion of the tubular body having greater lateral flexibility than the solid body.

2. A hybrid catheter guide wire as in claim 1 wherein the exterior surface of the tubular body includes a plurality of cuts spaced apart along at least a portion of the length of the tubular body to increase lateral flexibility thereof.

3. A hybrid catheter guide wire as in claim 2 wherein the longitudinal spacing between cuts is selectively varied to thereby selectively vary flexibility along at least a portion of the length of the tubular body.

4. A hybrid catheter guide wire as in claim 2 wherein the depth of the cuts is selectively varied to thereby selectively vary flexibility along at least a portion of the length of the tubular body.

5. A hybrid catheter guide wire as in claim 2 wherein at least some of the cuts are formed near the end of the tubular body farthest from the distal end of the solid body.

6. A hybrid catheter guide wire as in claim 2 wherein said cuts are formed by saw-cutting.

7. A hybrid catheter guide wire as in claim 2 wherein said cuts are formed by etching.

8. A hybrid catheter guide wire as in claim 2 wherein said cuts are formed by laser cutting.

9. A hybrid catheter guide wire as in claim 2 wherein said cuts are formed by electron discharge machining.

10. A hybrid catheter guide wire as in claim 1 wherein the guide wire further includes a radiopaque and/or MRI detectable element disposed at the distal end of the tubular elongate body.

11. A hybrid catheter guide wire as in claim 1 wherein the guide wire further includes a radiopaque and/or MRI detectable element disposed about at least a portion of the distal termination section, within the tubular body.

12. A hybrid catheter guide wire as in claim 1 wherein the solid body of material and tubular body of material are generally cylindrical.

13. A hybrid catheter guide wire as in claim 12 wherein the diameters of the solid body and tubular body are substantially the same.

14. A hybrid catheter guide wire as in claim 13 wherein said diameters are between about 0.008 inches to 0.035 inches.

15. A hybrid catheter guide wire as in claim 14 wherein said diameters are about 0.014 inches.

16. A hybrid catheter guide wire as in claim 15 wherein the diameter of the hollow of the tubular body is about 0.0085 inches.

17. A hybrid catheter guide wire as in claim 12 wherein the diameter of the solid body of material is greater than the diameter of the tubular body.

18. A hybrid catheter guide wire as in claim 12 wherein the diameter of the solid body of material is less than the diameter of the tubular body.

19. A hybrid catheter guide wire as in claim 1 wherein the solid body is made of stainless steel, and wherein the tubular body is made of nickel-titanium alloy.

20. A hybrid catheter guide wire as in claim 1 further including a lubricious coating disposed over the exterior of the tubular body.

21. A hybrid catheter guide wire as in claim 1 further including a lubricious sleeve disposed about the exterior of the solid body and tubular body.

22. A hybrid catheter guide wire as in claim 1 further including a sleeve disposed about the exterior of the solid body and tubular body, and a lubricious coating disposed over the exterior of the sleeve.

23. A hybrid catheter guide wire as in claim 1 wherein the thinner distal termination section of the solid body is co-extensive with and extends through the hollow of the tubular body.

24. A hybrid catheter guide wire as in claim 23 further including a plug disposed in a distal end of the tubular body and on the termination of the thinner distal termination section of the solid body.

25. A hybrid catheter guide wire as in claim 24 wherein the plug comprises a coil attached to the termination of the solid body and to the distal end of the tubular body.

26. A hybrid catheter guide wire as in claim 25 wherein said coil is made of a radiopaque or MRI detectable material.

27. A hybrid catheter guide wire as in claim 23 wherein the thinner distal termination section of the solid body is made of a material selected from the group consisting of polymers and fiber-reinforced materials.

28. A hybrid catheter guide wire as in claim 1 further including coil means disposed in the tubular body at least at the proximal end thereof, and about the proximal end thereof, and about at least a portion of the solid body at the thinner distal termination section thereof.

29. A hybrid catheter guide wire as in claim 28 wherein the coil means is attached to the tubular body and the solid body.

30. A hybrid catheter guide wire as in claim 28 wherein the coil means is made of platinum.

31. A hybrid guidewire configured for traversing a body lumen to a target location in a body of a patient, comprising:

an elongate core wire having a distal section of reduced profile; and, a tubular member disposed over at least a portion of the distal reduced profile section, said tubular member defining openings therein, and the tubular member being configured to be laterally relatively more flexible and torsionally relatively more stiff than at least a portion of the reduced profile distal section of the core wire, whereby a distal portion of the guidewire is configured, at a location where the guidewire includes the tubular member to enable transfer of a moment force from an adjacent proximal location along the guidewire toward a more distal location along the guidewire, and at the same time to minimize resistance to a lateral force tending to bend the guidewire distal portion, said tubular member being attached to the elongate core wire adjacent a proximal end of the tubular member and adjacent a distal end of the tubular member.

32. A hybrid guidewire as in claim 31, further comprising a marker coil disposed intermediate the tubular member and the core wire.

33. A hybrid guidewire as in claim 32, comprising a marker coil disposed adjacent the proximal end of the tubular member, and a marker coil disposed adjacent the distal end of the tubular member.

34. A hybrid guidewire as in claim 31, wherein a connection between the elongate core wire and the tubular member comprises solder.

35. A hybrid guidewire as in claim 31, wherein a connection between the elongate core wire and the tubular member comprises an adhesive.

36. A hybrid guidewire as in claim 31, wherein the holes in the tubular member are elongate and disposed so that their long dimension is transverse to a longitudinal axis of the guidewire.

* * * * *